(12) United States Patent
Sekoguchi et al.

(10) Patent No.: US 7,256,979 B2
(45) Date of Patent: Aug. 14, 2007

(54) ION GENERATOR, AND ELECTRIC APPARATUS AND AIR CONDITIONING APPARATUS INCORPORATING THE SAME

(75) Inventors: Yoshinori Sekoguchi, Nara (JP); Mamoru Morikawa, Yamatokooriyama (JP)

(73) Assignee: Sharp Kabushiki Kaisha, Osaka-Shi, Osaka (JP)

( * ) Notice: Subject to any disclaimer, the term of this patent is extended or adjusted under 35 U.S.C. 154(b) by 271 days.

(21) Appl. No.: 10/485,146

(22) PCT Filed: Jul. 31, 2002

(86) PCT No.: PCT/JP02/07834

§ 371 (c)(1),
(2), (4) Date: Jan. 29, 2004

(87) PCT Pub. No.: WO03/028179

PCT Pub. Date: Apr. 3, 2003

(65) Prior Publication Data

US 2004/0145853 A1    Jul. 29, 2004

(30) Foreign Application Priority Data

Aug. 1, 2001 (JP) ............................. 2001-234073
Oct. 12, 2001 (JP) ............................. 2001-315084

(51) Int. Cl.
*H01T 23/00* (2006.01)
(52) U.S. Cl. .................................................... 361/231
(58) Field of Classification Search ................ 361/229, 361/230, 231, 233, 235
See application file for complete search history.

(56) References Cited

U.S. PATENT DOCUMENTS

| 3,936,698 | A | | 2/1976 | Meyer ............................ 317/4 |
| 4,084,982 | A | * | 4/1978 | Prior et al. .................. 106/688 |
| 4,168,438 | A | * | 9/1979 | Morisue ...................... 250/574 |
| 4,423,462 | A | * | 12/1983 | Antonevich .................. 361/235 |
| 4,652,318 | A | * | 3/1987 | Masuda et al. .......... 156/89.19 |
| 4,740,862 | A | | 4/1988 | Halleck ....................... 361/231 |
| 4,757,422 | A | | 7/1988 | Bossard et al. ............. 361/231 |

(Continued)

FOREIGN PATENT DOCUMENTS

CN             2063705 U          10/1990

(Continued)

*Primary Examiner*—Stephen W. Jackson
*Assistant Examiner*—Scott Bauer
(74) *Attorney, Agent, or Firm*—Birch, Stewart, Kolasch & Birch, LLP

(57) ABSTRACT

A booster coil is stored in a coil storing room provided in the bottom section of a common case having an opening on one side, and is insulation-molded with a filler. A circuit substrate is inserted into the common case and supported by a supporting edge which is provided circumferentially at the middle of an inner wall of the common case. An ion generating element is held on a lid plate for closing the opening of the common case and mounted on the outer surface of the common case together with this lid plate, and the space between the circuit plate and the ion generating element is insulation-molded with a filler. An ion generator including the ion generating element and the booster coil and circuit substrate for generating a driving voltage is constructed in a compact size so as to enable the ion generator to be readily used in a wide range of applications.

26 Claims, 17 Drawing Sheets

U.S. PATENT DOCUMENTS

| | | | | |
|---|---|---|---|---|
| 4,918,568 | A | | 4/1990 | Stone et al. ................. 361/231 |
| 5,065,272 | A | * | 11/1991 | Owen et al. ................. 361/231 |
| 5,501,844 | A | * | 3/1996 | Kasting et al. ........ 422/186.15 |
| 5,576,923 | A | * | 11/1996 | Park ........................... 361/213 |
| 5,578,113 | A | * | 11/1996 | Glenn ............................ 96/52 |
| 5,677,511 | A | * | 10/1997 | Taylor et al. ................ 174/527 |
| 6,002,573 | A | * | 12/1999 | Partridge ..................... 361/231 |
| 6,039,816 | A | | 3/2000 | Morita et al. .................. 131/19 |
| 6,677,582 | B2 | * | 1/2004 | Yamada et al. ............. 250/288 |
| 2005/0284745 | A1 | * | 12/2005 | Smith ......................... 204/176 |

FOREIGN PATENT DOCUMENTS

| | | |
|---|---|---|
| EP | 0 345 498 A1 | 5/1989 |
| JP | 49-10872 | 1/1974 |
| JP | 50-88145 | 7/1975 |
| JP | 1-186180 A | 7/1989 |
| JP | 3-33823 Y2 | 7/1991 |
| JP | 4-090428 A | 3/1992 |
| JP | 6-31099 U | 4/1994 |
| JP | 6-62791 U | 9/1994 |
| JP | 07-130455 | 5/1995 |
| JP | 8-31230 A | 2/1996 |
| JP | 8-55692 A | 2/1996 |
| JP | 08-091807 A | 4/1996 |
| JP | 9-139277 A | 5/1997 |
| JP | 09-245934 A | 9/1997 |
| JP | 11-001304 A | 1/1999 |
| JP | 11-194581 A | 7/1999 |
| JP | 11-343104 A | 12/1999 |
| JP | 2000-133413 A | 5/2000 |
| JP | 2000-316225 A | 11/2000 |
| JP | 3077376 U | 2/2001 |
| JP | 2002-045685 A | 2/2002 |
| JP | 08-171979 A | 7/2004 |

* cited by examiner

ION GENERATOR, AND ELECTRIC APPARATUS AND AIR CONDITIONING APPARATUS INCORPORATING THE SAME

TECHNICAL FIELD

The present invention relates to an ion generator comprising an ion generating element for generating substantially equal amounts of positive ions and negative ions according to the application of a high-voltage AC driving voltage, and also relates to electric apparatuses and air conditioning apparatuses incorporating the ion generator. Examples of the above-mentioned electric apparatuses and air conditioning apparatuses include air conditioners, dehumidifiers, humidifiers, air purifiers, and fan heaters, and they are used mainly inside the rooms of houses, the rooms of buildings, the wards of hospitals, cars, air planes, ships, etc.

BACKGROUND ART

In recent years, as the airtightness in living space increases, there has been an increasing demand for the development of a technique to realize clean and comfortable living space, particularly a technique to purify the air inside the living space. For the purification of the air, conventionally, there are widely used air purifiers which are designed to produce a circulating air flow by sucking the air inside a target space and discharging the air through a suitable filter, and to catch floating substances present in this circulating air flow successively with the filter.

However, in this kind of air purifiers, floating substances are removed only from the air sucked into the main body, and thus it is difficult to give the air purifying effect throughout the living space. For example, there are problems that the air tends to stagnate behind furniture in a room, at the corners of a living room, or the like, and a sufficient effect cannot be expected in areas where air purification is necessary. Moreover, in order to maintain the satisfactory performance, cleaning and replacement of the filter are essential, and consequently there is a problem that complicated maintenance work including such cleaning and replacement must be performed.

Furthermore, the floating substances in the living room include particulates such as dust and smoke particles, and bacteria such as fungus and coli bacteria. Air purifiers using a filter as mentioned above are effective against the former matter (particulates) and can give a predetermined removal effect, but have a problem in terms of the latter matter (bacteria) harmful to human body, that is, a sufficient removal effect can not be obtained because the bacteria breed under the condition of being caught in the filter and are returned into the living space together with the circulating air flow. In recent years, air purifiers that improve the bacteria removal effect by using a filter made of antibacterial material have been put to practical use, but, in actual circumstances, satisfactory performances are not obtained.

In order to solve such problems, the applicant of the present application proposed a purifying method based on a new concept, in which the air in a space is purified by discharging ions into the space. This method is implemented by positioning an ion generator for generating substantially equal amounts of positive ions and negative ions, in the middle of a passage for discharging a flow of air into a target space, and discharging the positive ions and negative ions together with the flow of air into the target space.

Positive ions and negative ions are generated by ionizing moisture in the air by plasma discharge, and have a form in which a plurality of water molecules attach around hydrogen ions ($H^+$) or oxygen ions ($O_2^-$), i.e. the form of cluster ions. The ions discharged into the air gather around the floating particles, mutually cause a chemical reaction, make hydrogen peroxide $H_2O_2$ or hydroxy radical •OH as active species, carry out an oxidation reaction for removing hydrogen from the floating particles, inactivate the floating particles, and disinfect the floating bacteria.

Air purification as mentioned above is carried out by the function of ions which are discharged into the target space and spread throughout the space, and these ions act on the floating bacteria to disinfect them and further act on foul-smelling molecules and harmful molecules to make them odorless and harmless, thereby obtaining a satisfactory purification effect over the entire target space. Moreover, since the cluster ions discharged into the space are ions which are present in the natural world, harmless to human body and change to $H_2O$ (water) by oxidation reaction, there is no possibility that the cluster ions cause environmental pollution.

As described above, the ion generator for use in air purification performs the function of disinfecting floating bacteria, the function of making foul-smelling substances odorless, and the function of making harmful substances harmless. Therefore, there has been great demand for the application of the ion generator not only to air purifiers, but also to the whole range of electric apparatuses dealing with a flow of air, such as air conditioners, refrigerators and cleaners.

This ion generator comprises an ion generating element which has a discharge electrode and an induction electrode disposed to face each other with a dielectric therebetween and performs plasma discharge by application of a high-voltage AC driving voltage between the electrodes. This ion generating element can be constructed in a compact cylindrical shape in which the two electrodes are disposed on the center of the axis and the circumferential surface of a cylindrical dielectric, or in a compact plate shape in which the two electrodes are disposed on both surfaces of a plate-like dielectric. However, when this ion generating element is to be operated as the ion generator, it is necessary to provide booster means and a circuit substrate to increase the input voltage from a commercial power supply and generate a driving voltage having a predetermined driving waveform, and also necessary to ensure that their installed positions are mutually insulated. Thus, there are problems that it is difficult to apply this ion generating element to electric apparatuses other than those which were designed on the supposition that the ion generating element is to be incorporated into them, and the application range is limited.

DISCLOSURE OF THE INVENTION

The present invention has been made with the aim of solving the above problems and others, and it is a feature of the present invention to provide an ion generator capable of being constructed in compact size by combining an ion generating element for generating positive ions and negative ions according to the application of a high-voltage AC driving voltage with booster means and a circuit substrate for generating a driving voltage as a unit and of being readily used in a wide range of application, and also to provide electric apparatuses and air conditioning apparatuses using this ion generator.

Another feature of the present invention is to provide an ion generator capable of generating positive ions and negative ions in a stable manner, and also to provide electric apparatuses and air conditioning apparatuses using this ion generator.

An ion generator according to one aspect of the present invention is an ion generator comprising: an ion generating element for generating positive ions and negative ions by application of an AC driving voltage; booster means and a circuit substrate for generating a driving voltage to be applied to the ion generating element; and a housing (common case) having a storing room for the booster means and a supporting section for the circuit substrate, the housing integrally including a mounting section for mounting the ion generating element therein. In the present invention, the booster means, circuit substrate and ion generating element are configured as a unit by mounting them in the housing, thereby constructing a compact ion generator that can be easily used in a wide range of application by connecting it to an external power supply and control circuit.

Moreover, the housing (common case) is a box case having an opening in a part thereof, and includes the mounting section for the ion generating element in the periphery of the opening; the storing room for the booster means in an inner side of the housing, facing the mounting section; and the supporting section for the circuit substrate between the storing room and the mounting section. In this construction, with the use of the housing configured as a box case having an opening in a part thereof and a rational arrangement where the ion generating element is mounted in the periphery of the opening, the booster means is stored in the bottom section of the housing, facing the mounting section, and the circuit substrate is supported therebetween, a compact ion generator is realized.

Besides, the volume specific resistance of the housing (common case) is set to be equal to or higher than $1\times10^{16}$ $\Omega\cdot cm$. In this construction, it is possible to ensure satisfactory insulation for the housing, and generate positive ions and negative ions in a stable manner.

Moreover, the housing is molded using a resin material containing no carbon. In this construction, it is possible to ensure satisfactory insulation for the housing and generate positive ions and negative ions in a stable manner.

Further, the ion generating element comprises a discharge electrode and an induction electrode which face each other with a dielectric therebetween, and is mounted in the mounting section of the housing (common case) so that the discharge electrode side faces outward. In this construction, positive ions and negative ions are efficiently discharged by comprising the discharge electrode and induction electrode which face each other with the dielectric therebetween, using the compact ion generating element, and mounting the ion generating element on the housing with the discharge electrode side facing outward.

In addition, the ion generator comprises connecting means for supplying electric power to the booster means, integrally on the outside of the housing (common case). Furthermore, the mounting section for the ion generating element is provided substantially in parallel to the connecting direction to the connecting means. In this construction, the connecting means for external connection is provided integrally on the outside of the housing so as to facilitate connection with an external power supply and control circuit and improve the use of the ion generator. Additionally, the ion generating element is mounted on a surface substantially in parallel to the connecting direction to such connecting means so as to reduce the possibility that the ion generator is placed with the mounting surface of the ion generating element facing downward at the time of connection, and thereby preventing damages of the ion generating element.

Besides, the ion generator comprises supporting means for supporting the ion generating element at a distance from a suitable installation surface when the ion generator is installed on the installation surface with the mounting section for the ion generating element facing downward. In this construction, in the mounting stage to various kinds of apparatuses including connecting step to an external power supply and a control circuit, when the ion generator is installed on a suitable installation surface with the mounting section for the ion generating element facing downward, the ion generating element is supported at a distance from the installation surface, thereby preventing damages of the ion generating element due to contact with the installation surface.

Moreover, the mounting section for the ion generating element is provided on a lid plate for closing the opening of the housing (common case). In addition, the ion generating element is connected to the circuit substrate by lead wires passing through window holes piercing the lid plate. Furthermore, the ion generator comprises fastening parts for fastening the lead wires, on the peripheral edges of the window holes. In this construction, by providing the mounting section for the ion generating element on the lid plate for closing the opening of the housing and mounting the ion generating element in the opening together with the lid plate, it is possible to realize satisfactory mounting. In addition, by passing the lead wires for connecting the ion generating element and the circuit substrate through the window holes formed in the lid plate and connecting them satisfactorily and further fastening the lead wires with the fastening parts, it is possible to facilitate the running of the lead wires.

Besides, the booster means is insulation-molded with a first filler put in the storing room, while the space between the circuit substrate and the ion generating element is insulation-molded with a second filler put in the space therebetween. Moreover, the volume specific resistance of each of the first filler and second filler is set to be not less than $1\times10^{13}$ $\Omega\cdot cm$. Further, the first filler has a higher insulation strength than the second filler, while the second filler has a higher flowability than the first filler. In this construction, by providing insulation molding on the periphery of the booster means and in the space between the circuit substrate and the ion generating element by the fillers, respectively, a stable operation under a high driving voltage is realized. By setting the volume specific resistance of each of the first filler and second filler to be equal to or higher than $1\times10^{13}$ $\Omega\cdot cm$, positive ions and negative ions can be generated in a stable manner. In addition, by attaching great importance to the insulating strength when selecting a filler for the periphery of the booster means and attaching great importance to the flowability when selecting a filter for the space between the circuit substrate and the ion generating element, it is possible to realize satisfactory filling without creating gaps.

Additionally, the ion generator comprises a receiving room, provided beside the storing room for the booster means, for receiving/storing mounted components on the circuit substrate supported by the supporting section. Moreover, the ion generator comprises a bulkhead for separating the receiving room and the storing room from each other so as to prevent intrusion of the first filler and second filler. In this construction, the mounted components on the circuit substrate are received/stored in the receiving room provided beside the storing room for the booster means, and the separation distance between the circuit substrate and the ion generating element is reduced, thereby realizing a further compact ion generator. Furthermore, the bulkhead prevents the filler from acting on the mounted components on the circuit substrate received/stored in the receiving room, and thereby preventing application of stress to the mounted components due to the solidification/shrinkage of the filler.

Besides, the positive ions are $H^+(H_2O)_m$ (m is a natural number), and the negative ions are $O_2^-(H_2O)_n$ (n is a natural number). In this construction, the ion generating element generates cluster ions surrounded by a plurality of $H_2O$ molecules, and the ions inactivate floating particles and disinfect floating bacteria in a space into which the ions are to be emitted, thereby satisfactorily purifying the space.

Furthermore, in the present invention, an ion generator that is compact and easy to use is mounted in electric apparatuses and air conditioning apparatuses having an air passage for a flow of air, such as air conditioners, air purifiers, refrigerators and cleaners, so that the ion generator faces the air passage, and thereby purifying the air in the respective air passages and spaces into which a flow of air is emitted through the air passages.

BEST MODE FOR CARRYING OUT THE INVENTION

The following description will explain the present invention in detail with reference to the drawings illustrating some embodiments thereof.

Figure 1:
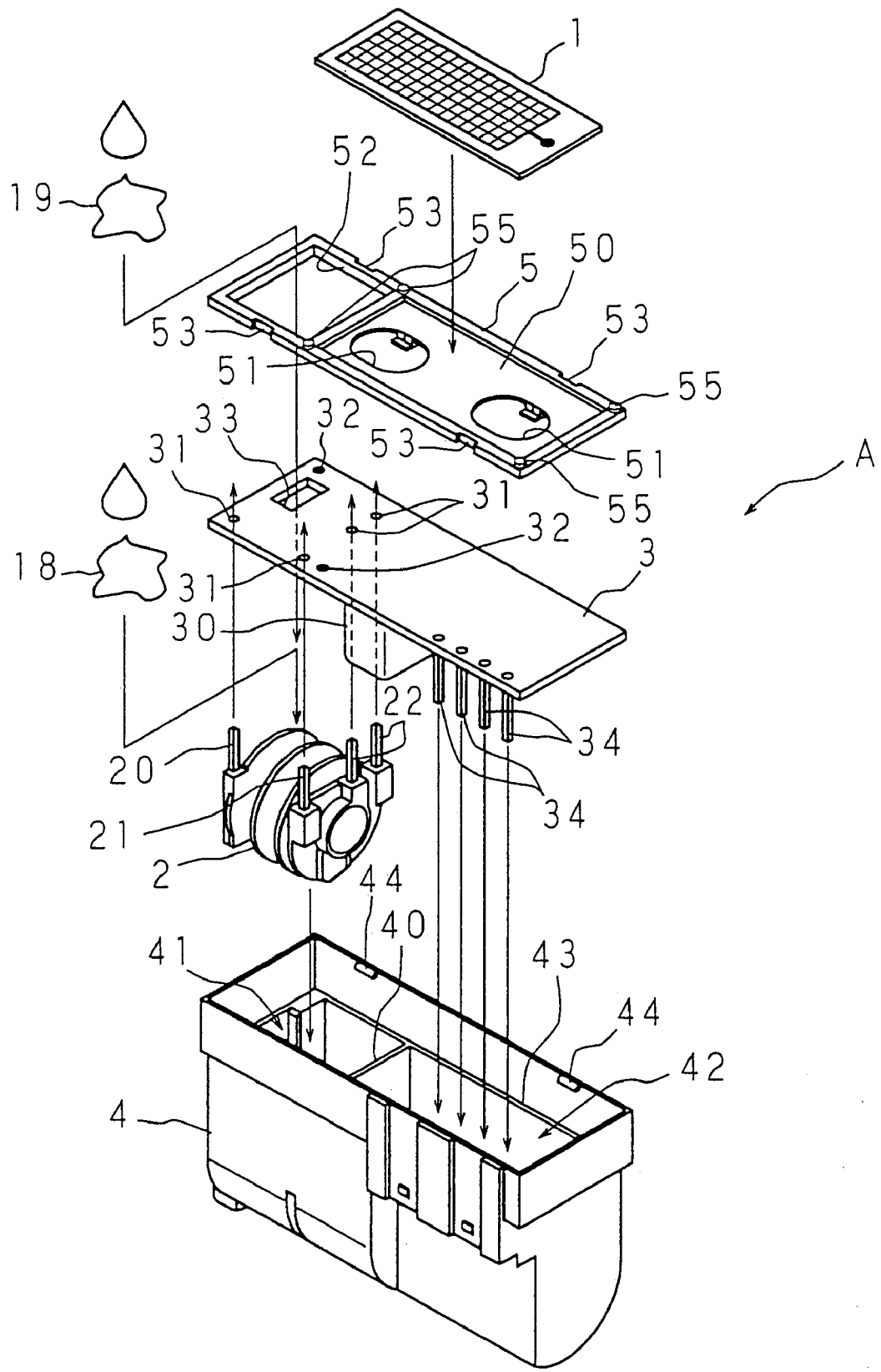
FIG. 1 is an exploded perspective view showing the first embodiment of an ion generator according to the present invention.
Figure 2:
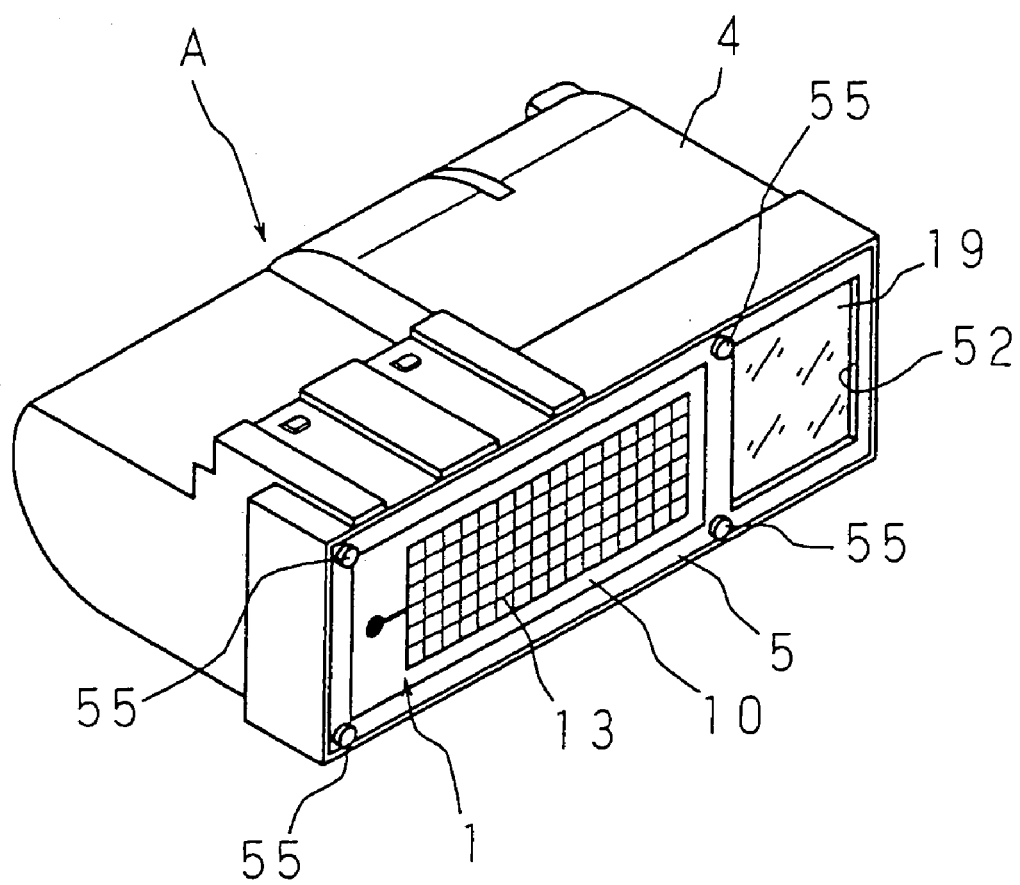
FIG. 2 is a perspective view of the appearance of the ion generator shown in FIG. 1, seen from the side on which the ion generating element is mounted.
Figure 3:
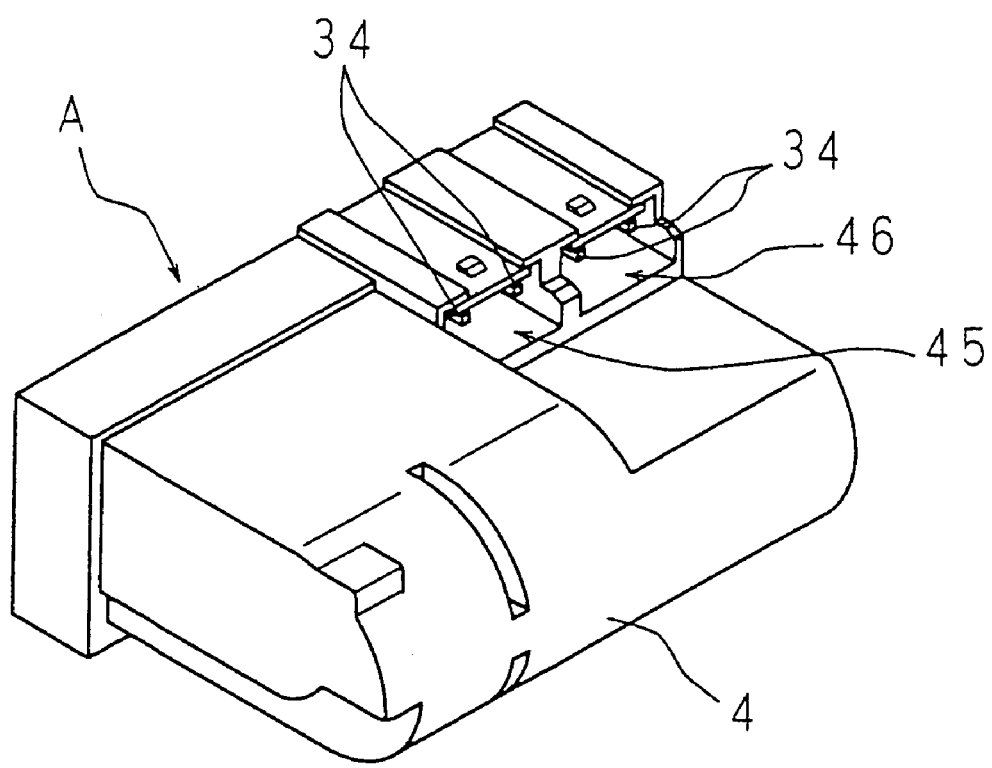
FIG. 3 is a perspective view of the appearance of the ion generator shown in FIG. 1 seen from the opposite side from FIG. 2.

FIG. 1 is an exploded perspective view showing the first embodiment of an ion generator according to the present invention; FIG. 2 is a perspective view of the appearance of the ion generator shown in FIG. 1, seen from the side on which the ion generating element is mounted; and FIG. 3 is a perspective view of the appearance of the ion generator shown in FIG. 1, seen from the opposite side from FIG. 2. As shown in FIG. 1, an ion generator A according to the present invention comprises a plate-like ion generating element 1, a booster coil (booster means) 2, a circuit substrate 3, a common case (housing) 4 for holding the above-mentioned components therein as a unit, and a lid plate 5 for holding the ion generating element 1 thereon and for closing the common case 4.

Figure 4:
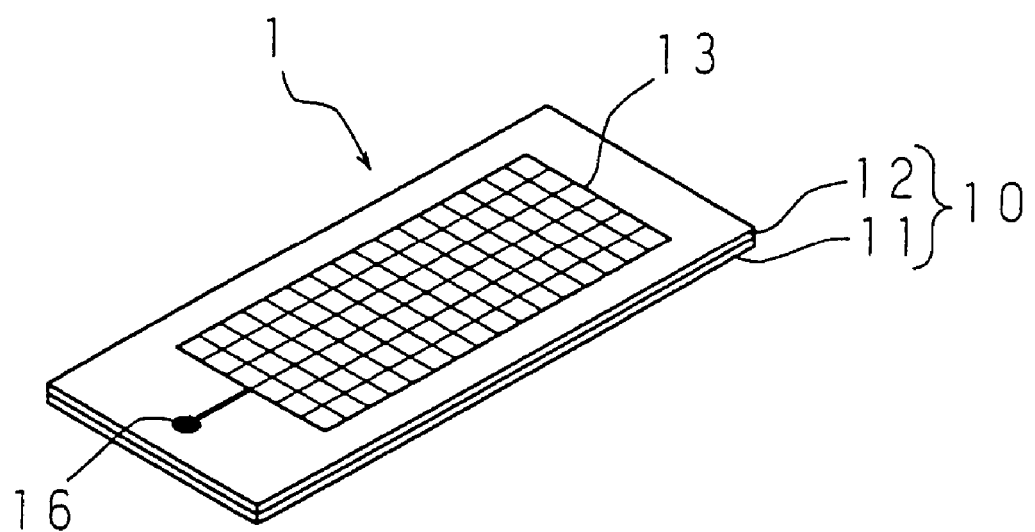
FIG. 4 is a perspective view of the appearance of an ion generating element.
Figure 5:
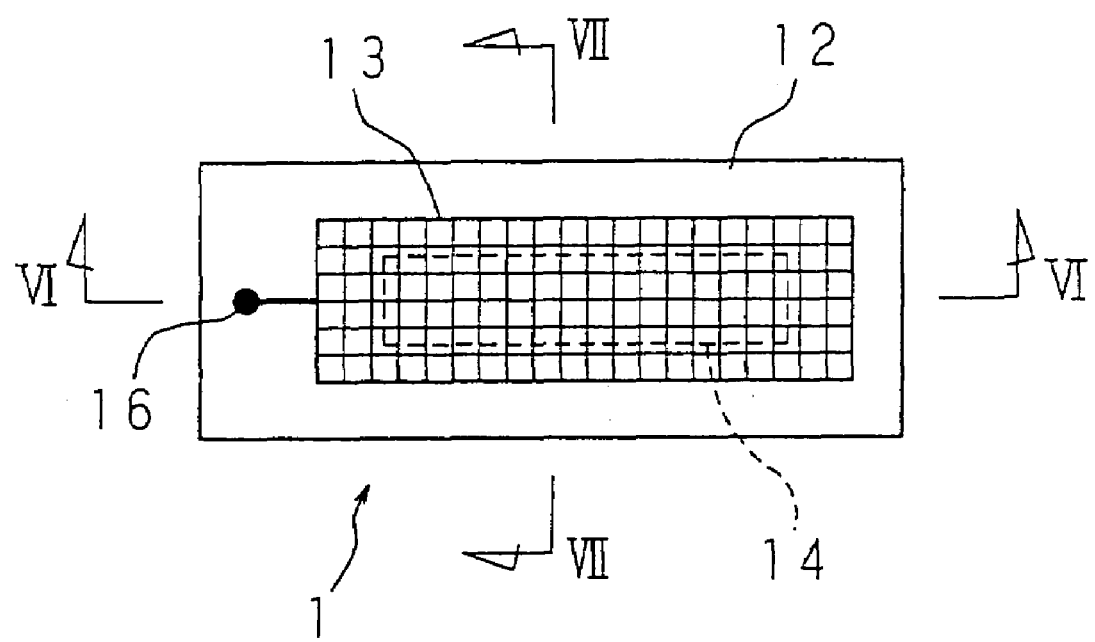
FIG. 5 is a plan view of the ion generating element.
Figure 6:
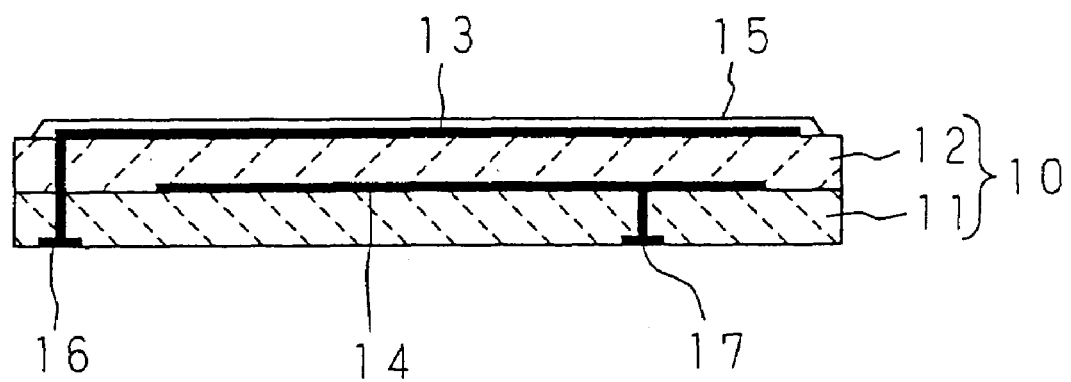
FIG. 6 is an enlarged cross sectional view cut along the VI-VI line.
Figure 7:
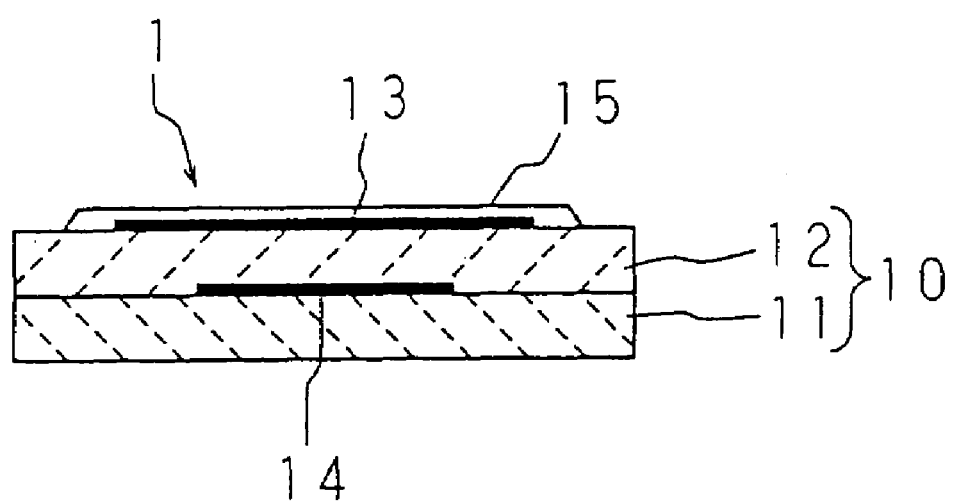
FIG. 7 is an enlarged cross sectional view cut along the VI-VII line.

FIG. 4 is a perspective view of the appearance of the ion generating element 1; FIG. 5 is a plan view of the ion generating element 1; FIG. 6 is an enlarged cross sectional view cut along the VI-VI line of FIG. 5; and FIG. 7 is an enlarged cross sectional view cut along the VII-VII line of FIG. 5. First, referring to these figures, the following description will explain the construction of the ion generating element 1.

The ion generating element 1 is constructed by forming a grid-like discharge electrode 13 on one surface of a dielectric substrate 10 produced by integrating a lower plate (lower dielectric) 11 and an upper plate (upper dielectric) 12 placed one upon another in the thickness direction as shown in FIGS. 4 and 5, burying a plane-like induction electrode 14 between the lower plate 11 and the upper plate 12 to face the discharge electrode 13 as shown in FIG. 5, and then covering the top of the discharge electrode 13 with a dielectric protective film 15 as shown in FIGS. 6 and 7.

For the lower plate 11 and upper plate 12 constituting the dielectric substrate 10, with the protective film 15, it is possible to use resin materials such as polyimide and epoxy, or ceramic materials such as alumina, crystallized glass, forsterite and steatite, but it is desirable to use ceramic materials having excellent heat resistance and strength, and more particularly alumina.

The discharge electrode 13 and the induction electrode 14 can be formed using metal materials which are ordinarily used for the formation of electrodes. However, in the case where the dielectric substrate 10 and the protective film 15 are made of ceramic materials, it is preferred that the discharge electrode 13 and the induction electrode 14 are made of metal materials having a high melting point, such as tungsten and molybdenum, in order to withstand the baking temperatures of the ceramic materials.

The ion generating element 1 as described above is obtained by, for example, forming the induction electrode 14 by pattern-printing a tungsten material on the front face of the lower plate 11 made of an alumina sheet, placing the upper plate 12 made of an alumina sheet to cover the entire surface of the formed induction electrode 14 and bonding them together by application of pressure, and then forming the discharge electrode 13 by pattern-printing the same tungsten material on the front face of the upper plate 12. Further, the protective film 15 made of alumina is formed by coating to cover the entire area where the discharge electrode 13 was formed, and finally they are baked at 1400 to 1600° C. under a non-oxidizing atmosphere.

As shown in FIG. 6, the discharge electrode 13 and the induction electrode 14 are connected to the rear face of the dielectric substrate 10 through an electrode contact 16 piercing the upper plate 12 and lower plate 11, and an electrode contact 17 piercing the lower plate 11, respectively, so that a high-voltage AC driving voltage is applied between the discharge electrode 13 and the induction electrode 14 through the electrode contacts 16 and 17. Note that the electrode contacts 16 and 17 can be formed integrally by filling through-holes formed in the corresponding positions with an electrode material in the processes for forming the electrodes 13 and 14, respectively.

As shown in FIGS. 4 and 5, the reason why the discharge electrode 13 is designed as a grid-like electrode is to increase, as quickly as possible, the amount of ions which are generated with the application of a driving voltage. Moreover, as shown in FIG. 5, the induction electrode 14 is formed as a strip electrode whose length and width are smaller than those of the discharge electrode 13 and whose center coincides with the center of the discharge electrode 13, and its shape is designed so that the projected area of the discharge electrode 13 is larger than the projected area of the induction electrode 14 so as to contribute to a balance of the yields of ions.

For instance, the grid-like discharge electrode 13 having a size of about 10.4 mm×28 mm was formed by arranging 0.25 mm wide lines perpendicularly and horizontally at a pitch of 0.8 mm on the front face of the dielectric substrate 10 having a size of about 15 mm×37 mm×0.9 mm, which was formed by stacking the lower plate 11 and the upper plate 12, both having a thickness of about 0.45 mm. Meanwhile, the plane-like induction electrode 14 having a size of about 6 mm×24 mm was formed between the lower plate 11 and the upper plate 12. When an approximately 4.6 kV (peak value) high-voltage AC driving voltage having a frequency of 22 kHz was applied between these electrodes, it was confirmed that positive ions and negative ions, both exceeding 200,000 ions/cc, were generated at a position 25 cm away from the ion generating element 1 by the function of plasma discharge that occurred between the electrodes 13 and 14. This yield of ions is sufficient to perform the function as an air purifier for an ordinary-size living room.

Note that the yield of ions increases with an increase in the size of the ion generating element 1 and also with an increase in the driving voltage. However, when the driving voltage is increased, the yield of ozone also increases, and therefore it is not desirable to increase the driving voltage excessively.

Moreover, the shapes of the discharge electrode 13 and induction electrode 14 and the size and thickness of the dielectric (upper plate 12) interposed therebetween are not necessarily limited to those used in the above-mentioned embodiment and can be changed suitably as long as the ion generating element 1 comprises a discharge electrode and an induction electrode which face each other with a plate-like dielectric therebetween and has a plate-like shape as a whole.

The ion generator A according to the present invention using the ion generating element 1 as mentioned above comprises the booster coil 2, circuit substrate 3, common case(housing) 4 and lid plate 5 as described above. As shown in FIG. 1, the booster coil 2 comprises a high-voltage terminal 20, a ground terminal 21 and a pair of input terminals 22 which are provided in a protruding manner on one side of a resin case.

The circuit substrate 3 is a substrate with a surface (the lower face in FIG. 1) on which a circuit for generating a driving waveform for the ion generating element 1 is formed and circuit components 30 (only one is shown) such as a capacitor and semiconductor are mounted. Four connection holes 31 for connecting the high-voltage terminal 20, the ground terminal 21 and the input terminals 22 of the booster coil 2 and connecting parts 32 for connecting the ion generating element 1 are provided on one side in the longitudinal direction of the circuit substrate 3 so as to correspond to the driving waveform generating circuit formed on the lower face, and a window hole 33 piercing the front and rear faces is formed inside the positions of the connection holes 31. Furthermore, provided on the other side of the circuit substrate are four connecting pins 34 for external connection, protruding from one surface.

The common case 4 is a box case having a rectangular opening for allowing insertion of the circuit substrate 3 over the entire surface on one side, and a bottom section with a semi-circular cross section on the other side. The bottom section is divided into a coil storing room 41 and a circuit components receiving room 42 by a bulkhead 40 with a predetermined height, placed laterally to cross the longitudinal direction at approximately right angles. Moreover, on the inner face of the common case 4, a supporting edge 43 to be a supporting section for the circuit substrate 3 is provided over the entire circumference to protrude inward, at a height position level with the upper edge of the bulkhead 40. Furthermore, in the peripheral edge of the opening of the common case 4, recesses 44 (only one side is shown) for locking the lid plate 5 are formed at two mutually separate positions in each of the longer sides facing each other.

As the material for this common case 4, it is preferable to select a resin material having an excellent electrical insulation property. For example, as in the case where the color tone of the common case 4 is to be made black, when the common case 4 is molded by mixing a pigment into a resin material, generally, carbon is added as the pigment. In such a case, however, since the volume specific resistance of the common case 4 is about $1 \times 10^9$ Ω·cm, it is impossible to ensure sufficient insulation for the respective structures inside the ion generator A. In contrast to the fact that positive ions and negative ions are generated in substantially equal amounts when sufficient insulation is ensured, the yield of ions generated by the ion generating element 1 at this time is 10,000 to 180,000 positive ions/cc and 200,000 to 430,000 negative ions/cc, causing a problem that an extremely large amount of negative ions are generated.

Hence, when the common case 4 is molded using a resin material to which carbon as a pigment is not added, the volume specific resistance of the common case 4 is about $1 \times 10^{16}$ Ω·cm or more, thereby ensuring sufficient insulation for the respective structures inside the ion generator A. At this time, the yield of ions is 190,000 positive ions/cc and 180,000 negative ions/cc, and thus substantially equal numbers of positive ions and negative ions are generated in a good balance. Note that examples of the resin material that provides the case with a volume specific resistance of $1 \times 10^{16}$ Ω·cm or more are PPE and PPS.

The lid plate 5 is a flat plate made of a resin material, and has a rectangular recession 50 corresponding to the ion generating element 1, on one side in the longitudinal direction thereof, and oval window holes 51 piecing the front and rear faces are formed in the recession 50, at positions corresponding respectively to the positions where the discharge electrode contact 16 and induction electrode contact 17 of the ion generating element 1 are formed. Moreover, a rectangular window hole 52 piercing the front and rear faces is formed on the other side in the longitudinal direction of the lid plate 5. Further, on both side edges in the width direction of the lid plate 5, locking claws 53 (only one side is shown) are formed at positions corresponding, respectively, to the recesses 44 formed in the peripheral edge of the opening of the common case 4.

The lid plate 5 configured as described above allows the ion generating element 1 to fit into the recession 50, thereby integrally holding the ion generating element 1. Fastening of the ion generating element 1 can be achieved by suitable means, such as bonding to the bottom face of the recession 50 and locking the peripheral edge of the ion generating element 1 with locking claws, not shown, provided on the periphery of the recession 50.

Note that the lid plate 5 has short leg projections 55 having a circular cross section on the four corners of the peripheral edge of the recession 50. When the lid plate 5 is mounted with the surface holding the ion generating element 1 facing down, these leg projections 55 ensure a predetermined clearance between the mounted surface and the ion generating element 1, and function as supporting legs for preventing damages of the ion generating element 1. This function can also be achieved by forming the recession 50 with a depth greater than the thickness of the ion generating element 1 and using the peripheral edges of the recession 50 as the supporting legs.

Figure 8:
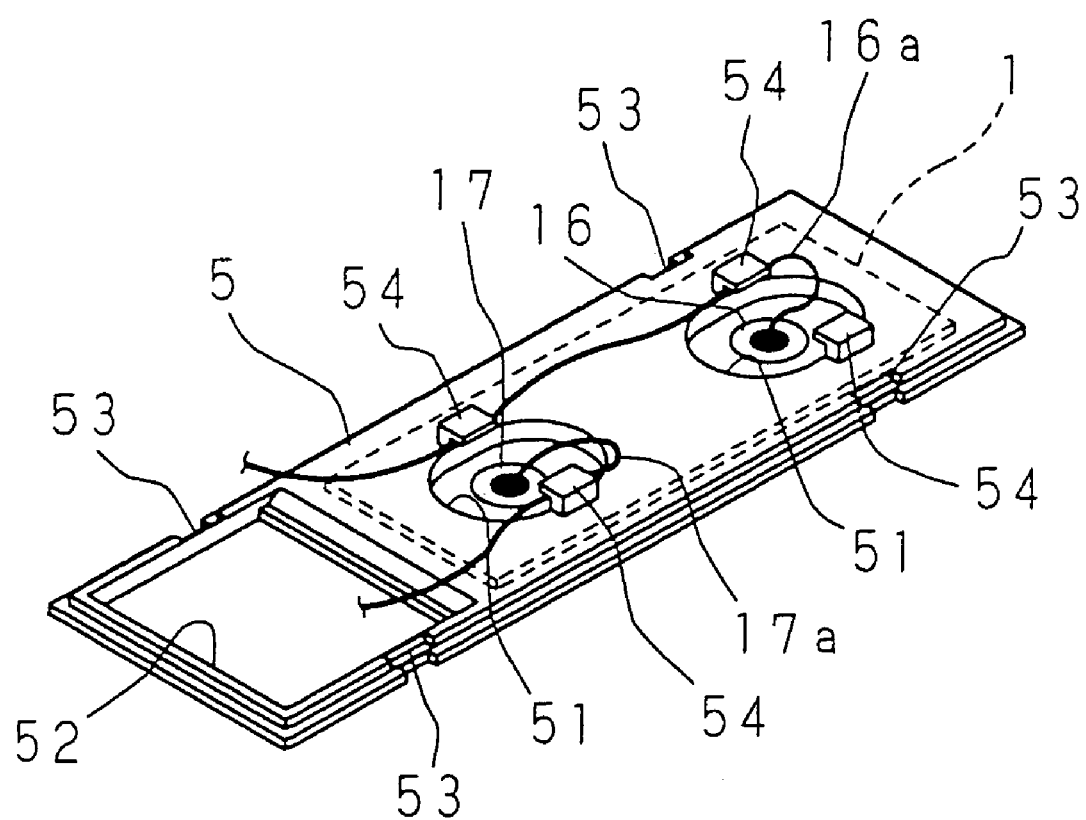
FIG. 8 is a perspective view seen from the rear-face side of a lid plate holding the ion generating element thereon.

FIG. 8 is a perspective view of the lid plate 5 holding the ion generating element 1, seen from the rear face. As described above, the window holes 51 formed in the recession 50 correspond to the exposed parts of the discharge electrode contact 16 and induction electrode contact 17 on the rear face of the ion generating element 1, and the ion generating element 1 is connected to the circuit substrate 3 with lead wires 16a and 17a welded to the electrode contacts 16 and 17, respectively. On the peripheral edge of each of the window holes 51, a pair of hook-like projections 54 are provided in the width direction, and the lead wires 16a and 17a are held by the hook-like projections 54 and guided with a distance between the lead wires 16a and 17a in the width direction toward the side on which the window hole 52 is formed for connection to the circuit substrate 3 as to be described later.

Since the hook-like projections 54 provided on the peripheral edges of the window holes 51 function as fastening parts for the lead wires 16a and 17a, it is possible to ensure a sufficient insulation distance between the lead wires 16a and 17a and easily run the wires lead wires 16a and 17a when connecting them to the circuit substrate 3.

The ion generator A according to the present invention is constructed by combining the above-configured booster coil 2, circuit substrate 3, common case 4, and lid plate 5 having the ion generating element 1 fixed thereto in the manner as described below.

First, the booster coil 2 is inserted into the coil storing room 41 provided in the bottom section of the common case 4 so that the protruding side of the high-voltage terminal 20, ground terminal 21 and input terminals 22 faces up, and insulation molding is performed by filling the coil storing room 41 with a filler 18 while preventing mixing of bubbles by vacuum suction. As the filler 18, it is desirable to use a resin material having an excellent insulation strength, such as an epoxy resin. Note that the filler 18 made of an epoxy resin is a resin material having excellent insulation properties with the specific volume resistance of about $1 \times 10^{13}$ $\Omega \cdot cm$. Moreover, if a part of the filler 18 is put into the coil storing room 41 prior to the insertion of the booster coil 2, it is possible to satisfactorily mold the outside of the booster coil 2 at the time of insertion of the booster coil 2 and effectively prevent occurrence of insulation defects due to mixing of bubbles. Furthermore, the filler 18 should be put into only the coil storing room 41, and care must be taken to avoid leakage of the filler 18 into the circuit components receiving room 42 located next to the coil storing room 41 with the bulkhead 40 therebetween.

Then, after waiting for the filler 18 to dry and solidify, the circuit substrate 3 is inserted into the common case 4 through the upper-side opening. This insertion is performed by directing the surface on which the circuit components 30 are mounted downward, positioning the four connection holes 31 for connection to the booster coil 2 above the booster coil 2 fixed to the coil storing room 41, and inserting the circuit substrate 3 until the lower face thereof hits the bulkhead 40 and the supporting edge 43. After the insertion, the tips of the high-voltage terminal 20, ground terminal 21 and input terminals 22 protruding from the connection holes 31 are welded to the corresponding positions from the upper face of the circuit substrate 3.

With this welding, the circuit substrate 3 is supported from the lower side by the supporting edge 43 and the upper edge of the bulkhead 40, and the high-voltage terminal 20, ground terminal 21 and input terminals 22 are fixed as the supporting legs by the booster coil 2 fixed by the filler 18. At this time, the circuit components 30 mounted on the circuit substrate 3 are received/stored in the circuit components receiving room 42 provided beside the coil storing room 41, while the four connecting pins 34 protruding from one edge on the same side protrude toward the outside of the common case 4 through the openings provided in the corresponding positions, thereby constructing the connection terminals 45 and 46 (see FIG. 3) for connection to an external power supply and an external control circuit. Note that the distances between two connecting pins 34 of each of the connection terminals 45 and 46 are made different from each other so as to avoid occurrence of mistaken connections.

After mounting the circuit substrate 3 in the above-mentioned manner, the lid plate 5 holding the ion generating element 1 as described above is mounted. The mounting is carried out by aligning the window hole 52 formed on one side in the longitudinal direction with the position of the window hole 33 formed in the circuit substrate 3 which was fastened in the common case 4 in advance; positioning the lid plate 5 on the top-side opening of the common case 4 with the surface holding the ion generating element 1 facing up; welding the lead wires 16a and 17a of the ion generating element 1 running along the rear face of the lid plate 5 as described above respectively to the connection sections 32 provided on the upper face of the circuit substrate 3; and then fitting the lid plate 5 into the top-side opening of the common case 4. At this time, the locking claws 53 provided on both side edges of the lid plate 5 are deflected/deformed, locked with the corresponding recesses 44 provided on the peripheral edge of the opening of the common case 4 by resilient return, and consequently the lid plate 5 is mounted at a position separated from the upper face of the circuit substrate 3 by a suitable distance to cover the opening of the common case 4.

After the mounting, a filler 19 is introduced through the window hole 52 formed in the lid plate 5 to fill the space between the lid plate 5 and the circuit substrate 3 with the filler 19, and the space between the circuit substrate 3 and the ion generating element 1 is insulation-molded. Then, after waiting for this filler 19 to dry and solidify, the ion generator A according to the present invention is constructed as shown in FIGS. 2 and 3.

As the filler 19, in order to perform satisfactory filling through the window hole 52, it is desirable to use a resin having an excellent flowability, such as a urethane resin. Note that a part of the filler 19 is also put into the upper section of the coil storing room 41 storing the booster coil 2 through the window hole 33 of the circuit substrate 3 which opens at a position below the window hole 52, and functions to assist the insulation by the filler 18. Moreover, at this time, although the filler 19 tries to intrude into the circuit components receiving room 42 located beside the coil storing room 41, this intrusion is blocked by the bulkhead 40 between the two rooms 41 and 42. Accordingly, the mounted components on the circuit substrate 3 received/stored in the circuit components receiving room 42 are free from stress caused by the shrinkage of the filler 19 during solidification, thereby preventing occurrence of defects such as disconnection and detachment.

On the other hand, the stress caused by the shrinkage of the filler 19 is also applied to the lead wires 16a and 17a of the ion generating element 1, drawn to the lower face of the lid plate 5. However, since these lead wires 16a and 17a are held by the hook-like projections 54 provided on the peripheral edges of the window holes 51 for drawing as described above, the welded section between the ion generating element 1 and the circuit substrate 3 is not affected by the stress, thereby maintaining a satisfactorily connected state.

The ion generator A constructed as described above is designed in a compact configuration with the ion generating element 1 mounted on the outside of the common case 4 including the booster coil 2 and the circuit substrate 3 therein, and can perform an ion generating operation by connecting the connection terminals 45 and 46 to an external power supply and an external control circuit, and can be easily incorporated for use in various types of electric apparatuses which require air purification. Needless to say, the range of the electric apparatuses includes apparatuses which require purification of air to be emitted to the outside, such as air purifiers and air conditioners, but also includes electric apparatuses which require purification of air circulating in the inside (in the room), such as refrigerators, and electric apparatuses which demand purification of air to be discharged to the outside, such as cleaners. Hence, the ion generator A can be used for a wide range of electric apparatuses.

Figure 9:
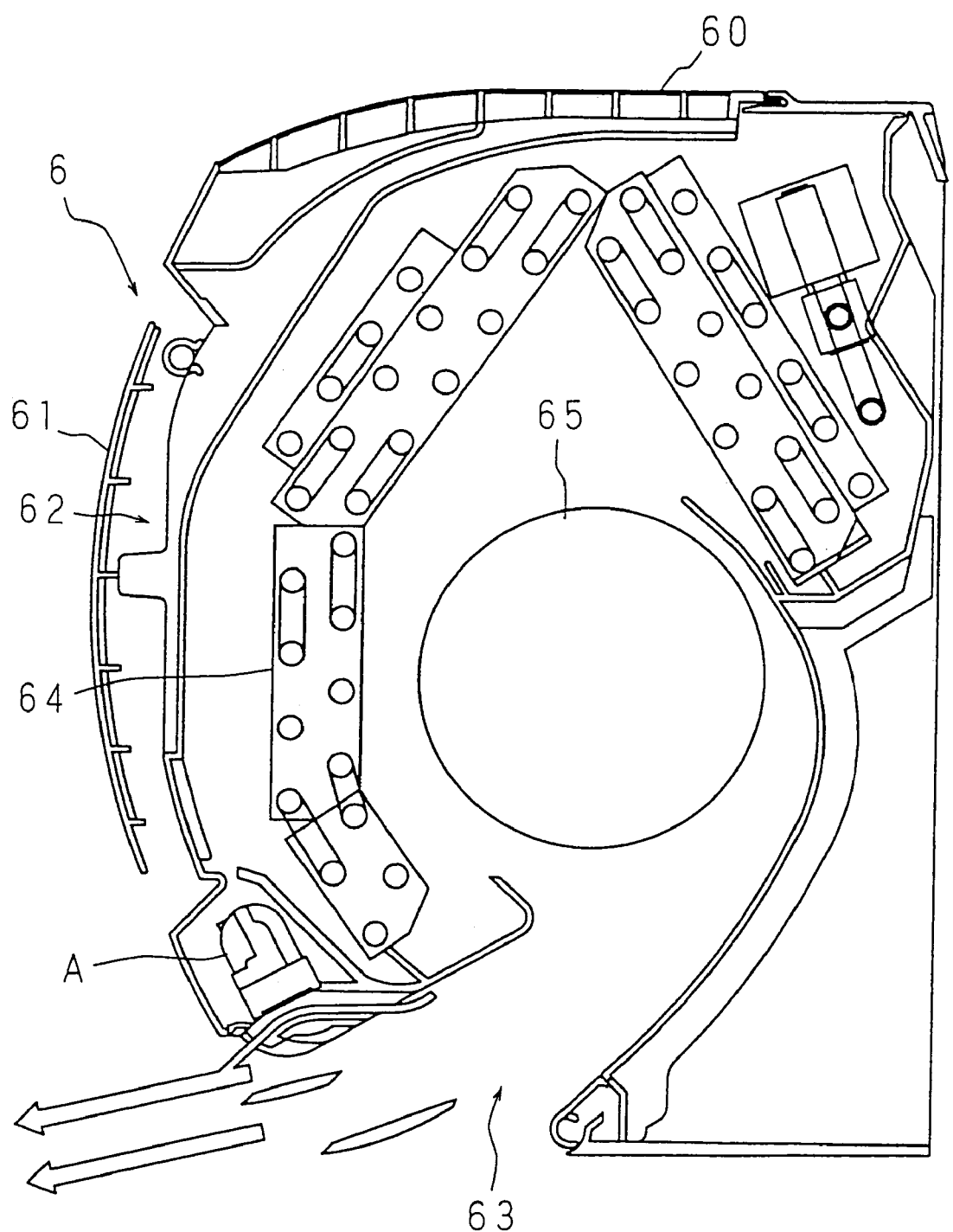
FIG. 9 is a cross sectional side view showing an example of the application of an ion generator of the present invention to an air conditioner.
Figure 10:
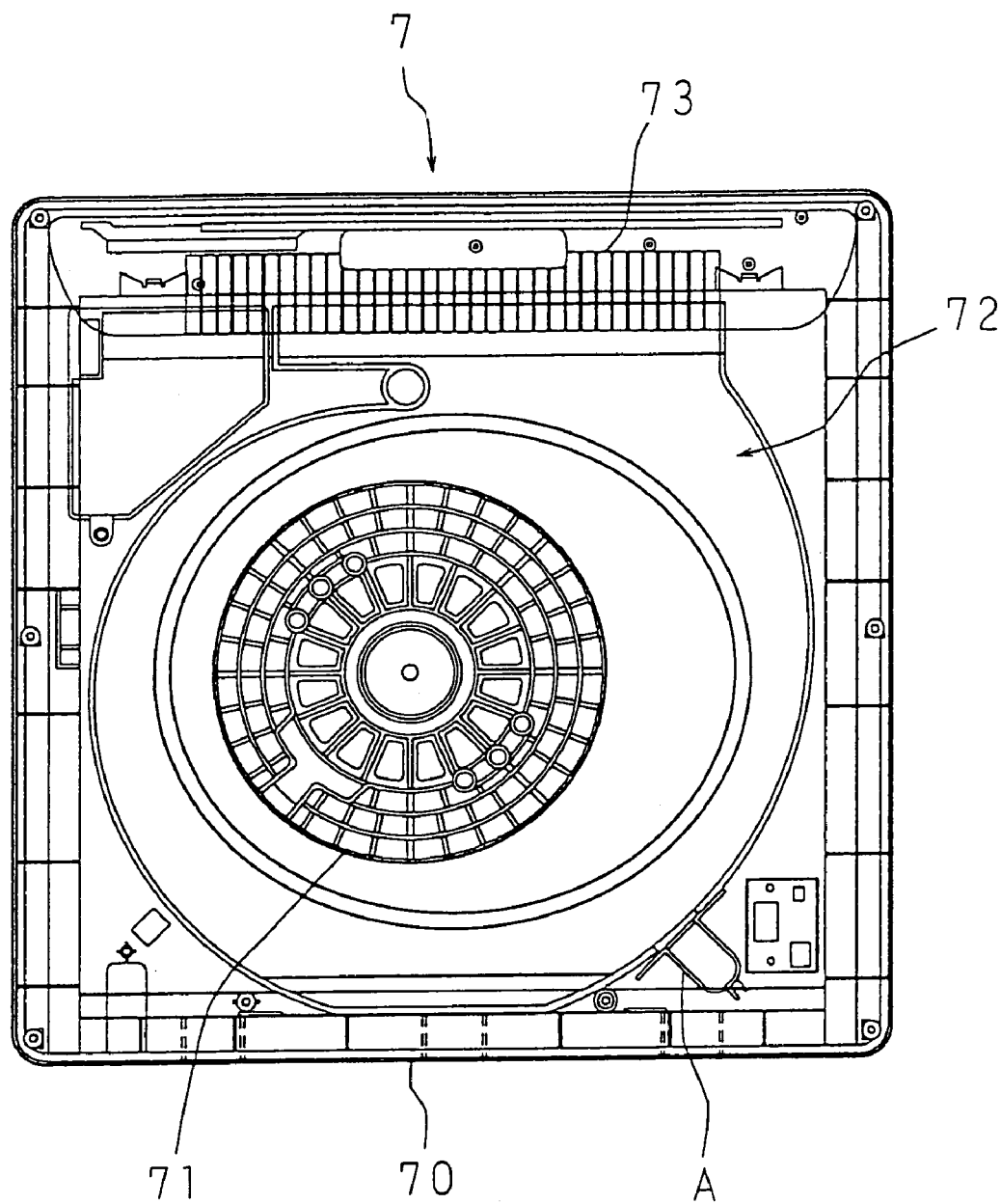
FIG. 10 is a cross sectional front view showing an example of the application of an ion generator of the present invention to an air purifier.

FIG. 9 is a cross sectional side view showing an example of the application of an ion generator of the present invention to an air conditioner, and FIG. 10 is a cross sectional front view showing an example of the application of the ion generator to an air purifier.

As shown in FIG. 9, an air conditioner 6 comprises: an inlet 62, which is covered with a front panel 61 having a number of slits or holes so that it is freely open and closed, in the upper part of the front face (the left face in FIG. 9) of a main body housing 60; an outlet 63 in the lower part of the front face; a heat exchanger 64 and a fan 65 placed side by side in the middle of a curved air passage formed inside the main body housing 60 to connect the inlet 62 and the outlet 63 together. The air conditioner 6 sucks air from the inlet 62 with a rotation of the fan 65, cools down or heats the air by contact with the heat exchanger 64, and blows out the air from the outlet 63 as shown by the open arrows in FIG. 9.

In such an air conditioner 6, the ion generator A according to the present invention is positioned deep inside the outlet 63, and mounted so that the mounting surface of the ion generating element 1 faces a flow of air in the air passage. After the mounting, when the connection terminals 45 and 46 (see FIG. 3) outside the common case 4 are connected to an external power supply and the control circuit of the air conditioner 6, the ion generator A ionizes moisture in the air blew out from the outlet 63 by plasma discharge, and generates and sends out substantially equal amounts of positive ions and negative ions.

Here, the positive ion is a cluster ion in which a plurality of water molecules attach around a hydrogen ion ($H^+$), and is denoted as $H^+(H_2O)_m$ (m is a natural number). Besides, the negative ion is a cluster ion in which a plurality of water molecules attach around an oxygen ion ($O_2^-$), and is denoted as $O_2^-(H_2O)_n$ (n is a natural number). After these positive ions and negative ions are emitted from the outlet 63, as mentioned above, they gather around the floating substances (particles and bacteria) in the space into which they were emitted, mutually cause a chemical reaction, generate hydrogen peroxide $H_2O_2$ or hydroxy radical OH as active species, and perform the functions of inactivating the floating particles and disinfecting the floating bacteria by the oxidation reaction, thereby purifying the inside of the room where the air conditioner 6 is installed.

As shown in FIG. 10, an air purifier 7 has an inlet covered with a filter 71, deep inside a main body housing 70, and a fan (not shown) installed deep inside from the filter 71. A spiral air passage 72 is formed in front of the filter 71 and connected to an outlet 73 formed in the upper part of the main body housing 70. The air purifier 7 sucks air from the inlet with a rotation of the fan, catches the floating substances contained in the air with the filter 71, causes the air to flow in the spiral air passage 72, and sends out the air from the outlet 73.

In such an air purifier 7, the ion generator A according to the present invention is mounted on a part of the circumferential wall of the air passage 72 so that the mounting surface of the ion generating element 1 faces the air flowing in the air passage 72. After the mounting, when the connection terminals 45 and 46 (see FIG. 3) outside the common case 4 are connected to an external power supply and the control circuit of the air purifier 7, the ion generator A ionizes moisture in the air flowing in the air passage 72 by plasma discharge, and performs the operation of generating substantially equal amounts of positive ions and negative ions. These ions are emitted together with the air from the outlet 73, and perform the functions of inactivating the floating particles and disinfecting the floating bacteria in the space into which the ions were emitted as described above. Accordingly, the inside of the room where the air purifier 7 is installed can be purified by the synergistic effect with the catching of dust by the filter 71.

Figure 11:
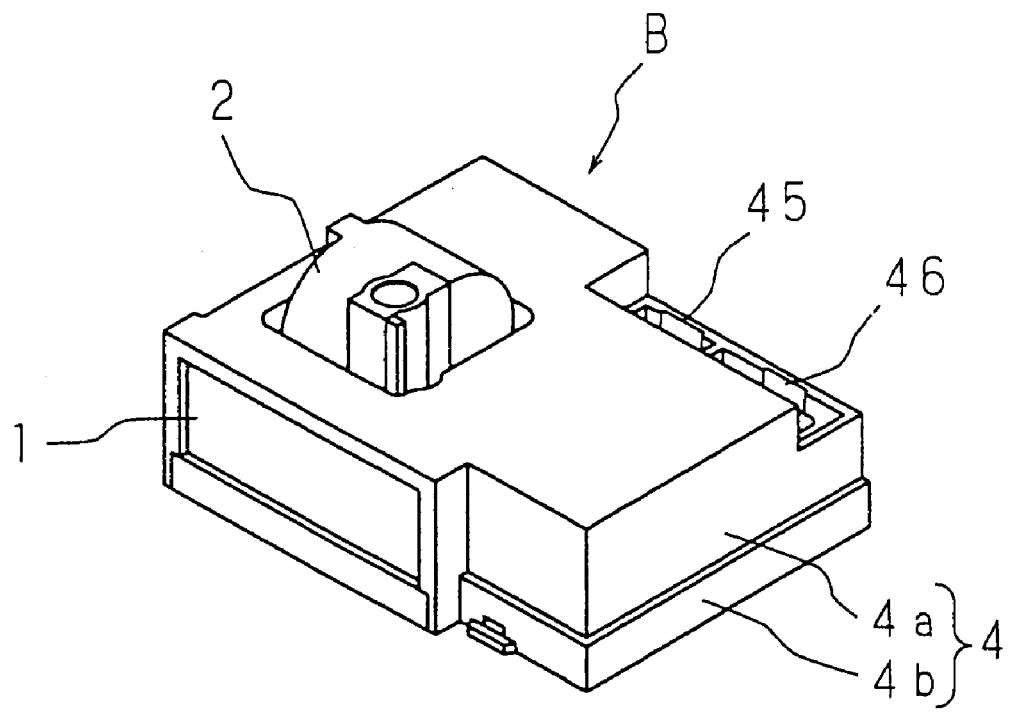
FIG. 11 is a perspective view showing the appearance of the second embodiment of an ion generator according to the present invention.
Figure 12:
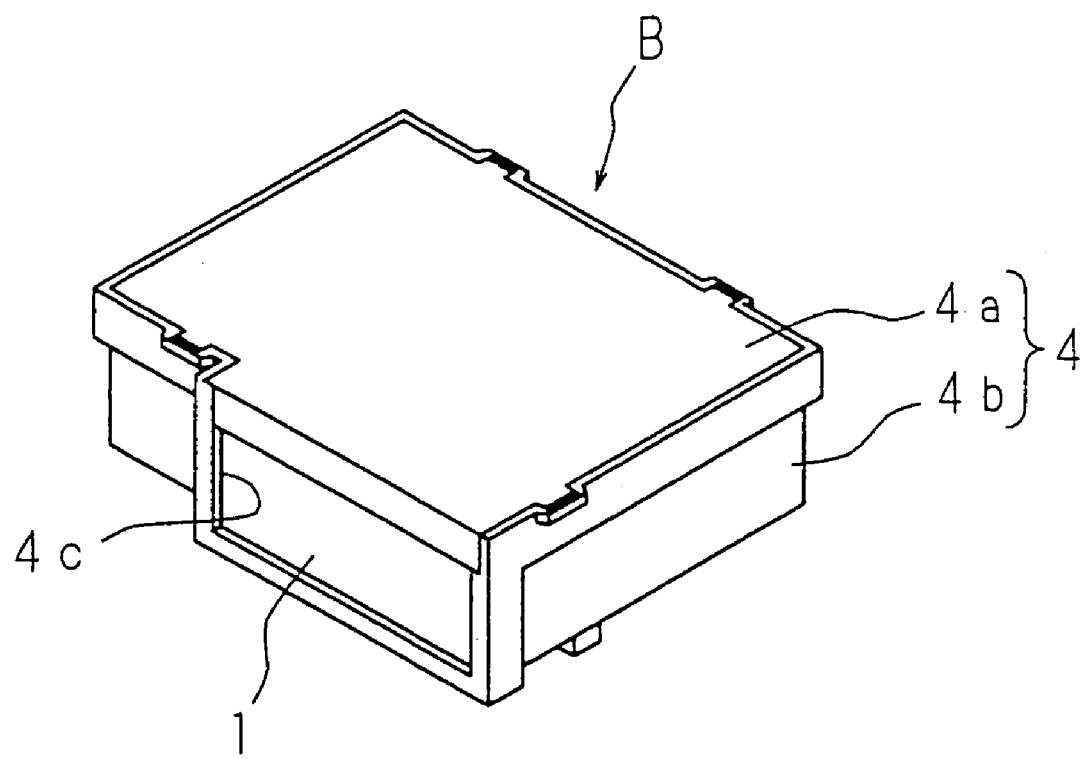
FIG. 12 is a perspective view of the appearance seen from the lower side of FIG. 11.

FIG. 11 is a perspective view showing the appearance of the second embodiment of an ion generator according to the present invention, and FIG. 12 is a perspective view of the appearance seen from the lower side of FIG. 11. Like the ion generator A of the first embodiment, an ion generator B shown in FIGS. 11 and 12 comprises a plate-like ion generating element 1, a booster coil 2, a circuit substrate 3 (see FIG. 13), and a common case 4 for holding these components as a unit. This ion generator B is characterized by providing a mounting section for the ion generating element 1 on a surface substantially in parallel to the direction of the connection terminals 45 and 46 provided on the outside of the common case 4 for connection to an external power supply and an external control circuit.

The common case 4 is constructed by combining an upper case 4a and a lower case 4b to be placed one upon another. The connection terminals 45 and 46 are provided along one side edge of the upper case 4a, and the ion generating element 1 is mounted along a side edge facing the above-mentioned one side edge. Note that, in FIGS. 11 and 12, illustration of the discharge electrode 13 formed on the front face of the ion generating element 1 as shown in FIGS. 4 and 5 is omitted.

In this construction, as shown in FIG. 11, in the state where the ion generator B is installed so that the connection terminals 45 and 46 are to be inserted in an upward direction, the front face of the ion generating element 1 does not come into contact with the surface where the ion generator B is installed when connecting the connection terminals 45 and 46 to the external power supply and control circuit, thereby preventing damages of the ion generating element 1 due to the contact.

Note that, in the embodiment illustrated in FIGS. 1 through 3, during the connection process performed by installing the ion generator B so that the connection terminals 45 and 46 are to be inserted in an upward direction, the four leg projections 55 provided on the peripheral edge of the recession 50 holding the ion generating element 1 thereon support the ion generating element 1 facing downward, in a floating state with a space between the front face thereof and the installation surface, thereby performing the function to prevent damages of the ion generating element 1.

Figure 13:
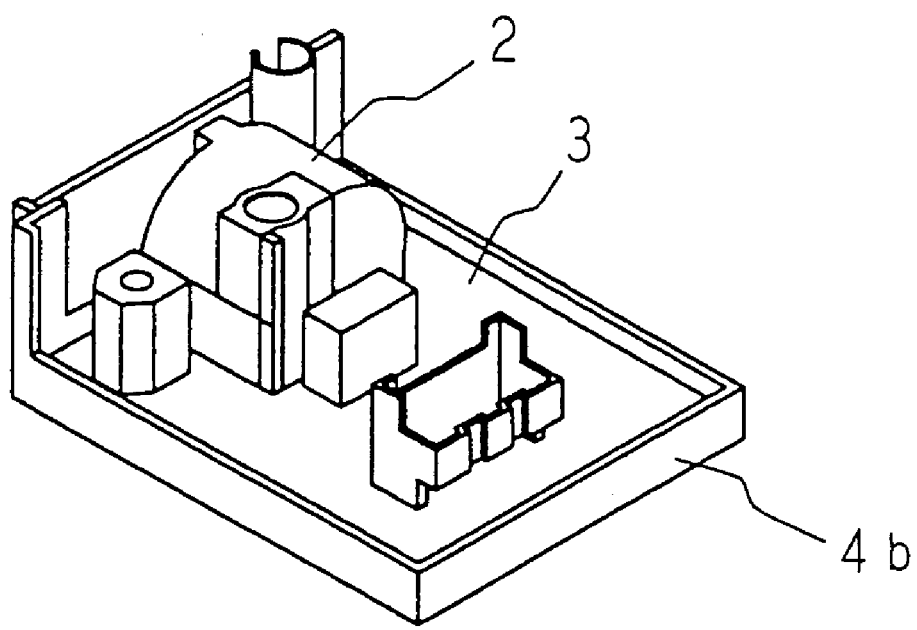
FIG. 13 is a perspective view showing an example of the arrangement of a booster coil and a circuit substrate inside a housing (common case)

FIG. 13 is a perspective view showing an example of the arrangement of the booster coil 2 and the circuit substrate 3 in the common case 4 with the upper case 4a removed. As shown in FIG. 13, the circuit substrate 3 is installed over substantially the entire surface of the bottom section of the lower case 4b, and the booster coil 2 is disposed on one side in the longitudinal direction of the circuit substrate 3.

Figure 14:
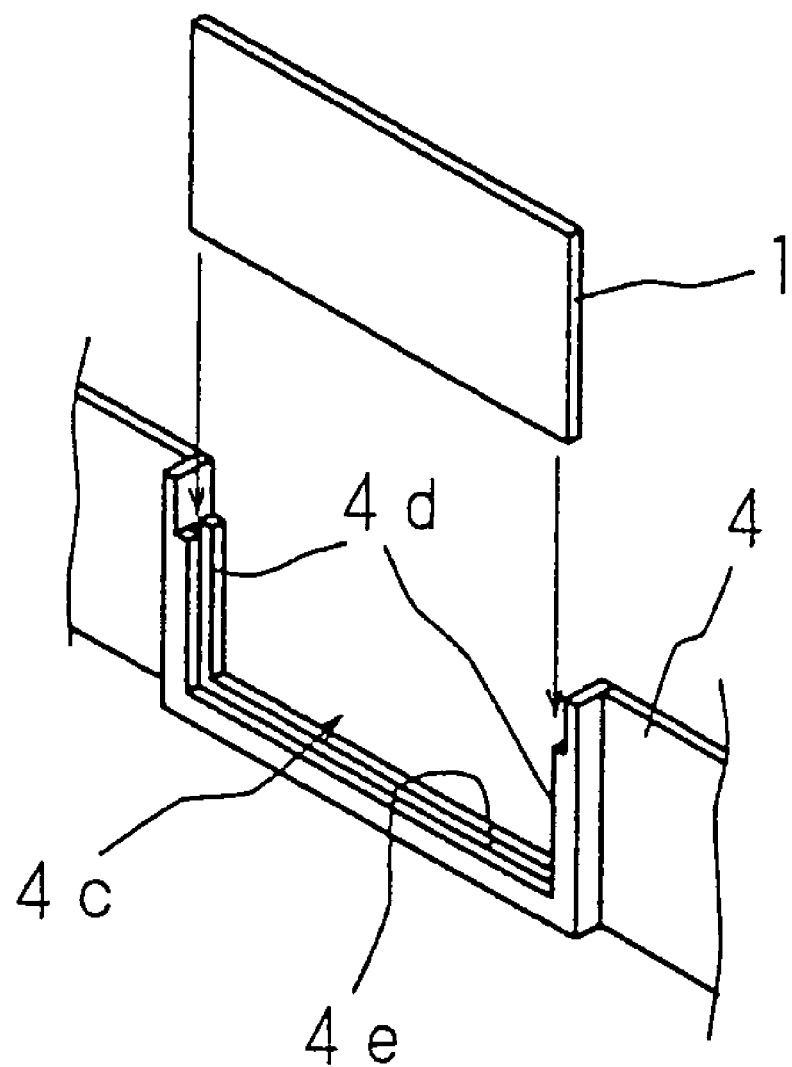
FIG. 14 is a perspective view showing an example of the structure of a window hole for mounting the ion generating element.

The ion generating element 1 is mounted in a window hole 4c formed in a side face of the upper case 4a. FIG. 14 is a perspective view showing an example of the structure of the window hole 4c. As shown in FIG. 14, the window hole 4c is formed to a height substantially equal to the overall height of the side face by cutting a portion of the side face of the upper case 4a, equivalent to the length of the ion generating element 1, and vertical grooves 4d and a horizontal groove 4e are formed with a width equivalent to the thickness of the ion generating element 1 on the peripheral edge surrounding the three sides thereof. The window hole 4c can be placed in position by bringing both of the short sides of the ion generating element 1 into engagement with the vertical grooves 4d, pushing the ion generating element 1 by using the vertical grooves 4d as guides, and bringing one long side into engagement with the horizontal groove 4e. By pressing the remaining one long side with the edge of the lower case 4b to be combined with the upper case 4a, the ion generating element 1 is mounted as shown in FIGS. 11 and 12.

Figure 15:
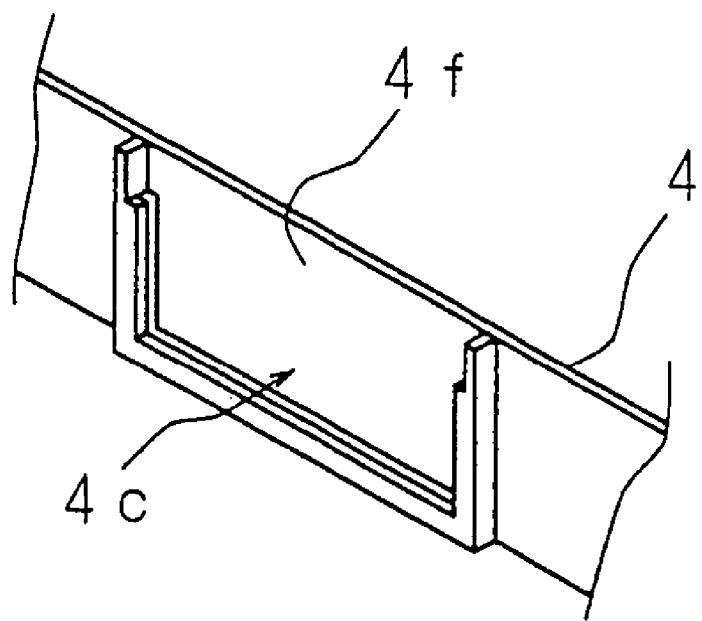
FIG. 15 is a perspective view showing another example of the structure of a window hole for mounting the ion generating element.

FIG. 15 is a perspective view showing another example of the structure of the window hole 4c. The window hole 4c shown in FIG. 15 is formed with a thin removable piece 4f left on a side face of the upper case 4a. By removing the removable piece 4f when mounting the ion generating element 1, the vertical grooves 4d and horizontal groove 4e as shown in FIG. 14 are formed. According to this structure, by forming window holes 4c in the four sides of the upper case 4a and cutting off the removable piece 4f of a window hole 4c according to the need of the application, it is possible to suitably select a mount position having a desired positional relation with the connection terminals 45 and 46 and selectively use the window hole 4c according to the application.

Figure 16:
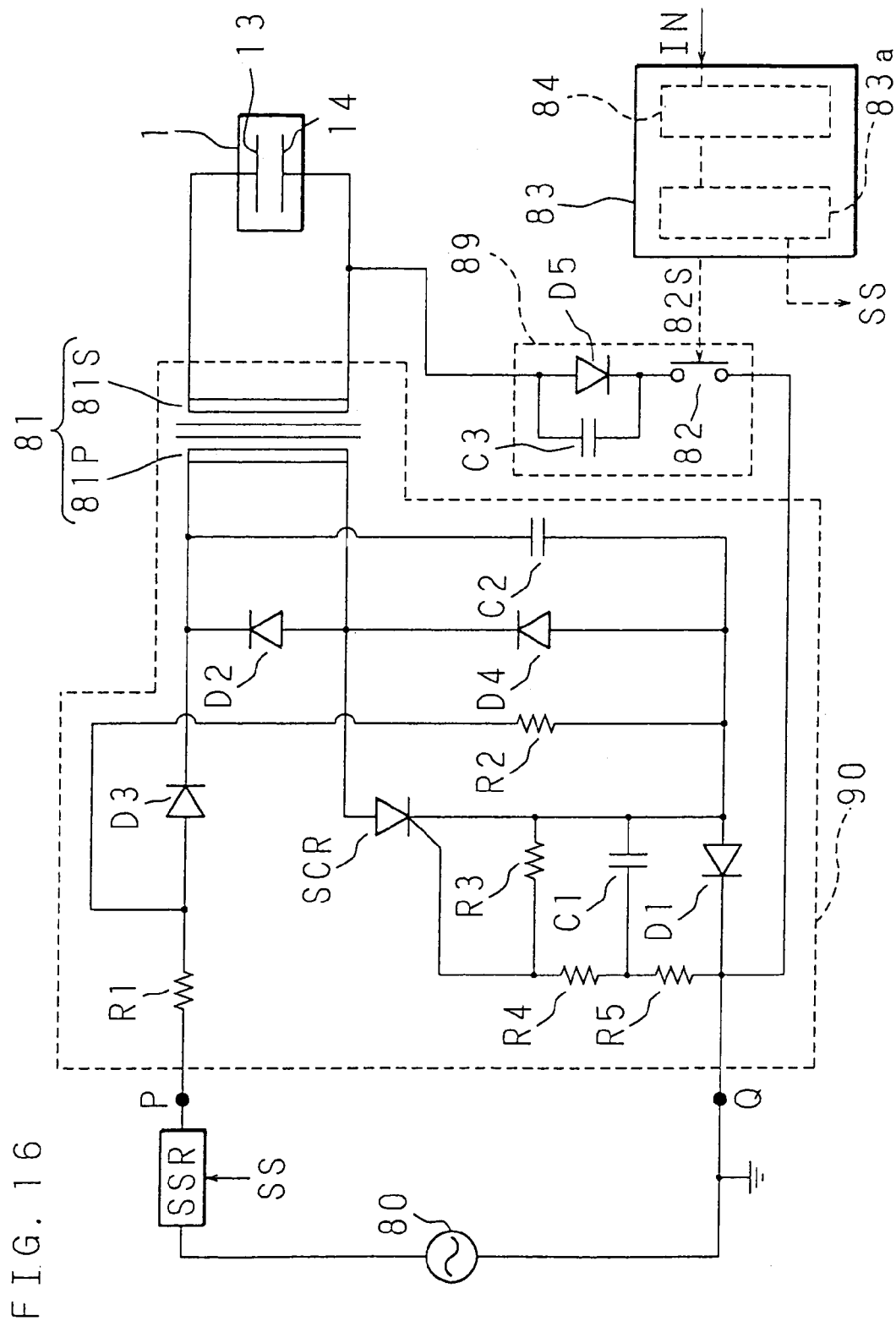
FIG. 16 is an essential circuit diagram of an ion generator according to the present invention.
Figure 17:
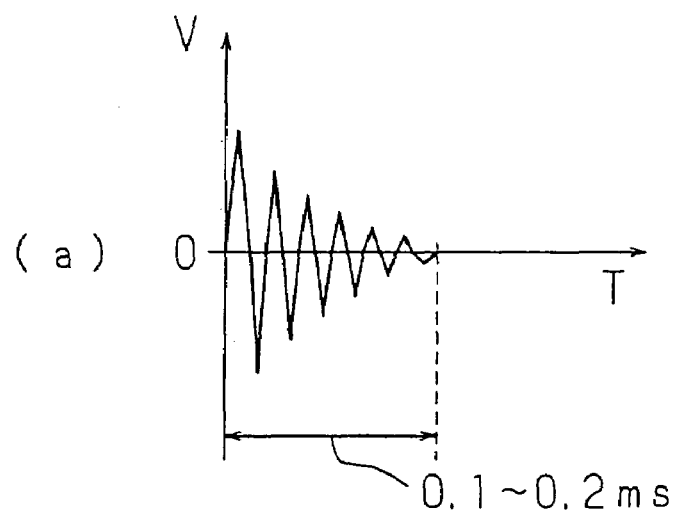
FIG. 17 is an electric potential waveform view of the ion generating element of FIG. 16.
Figure 17:
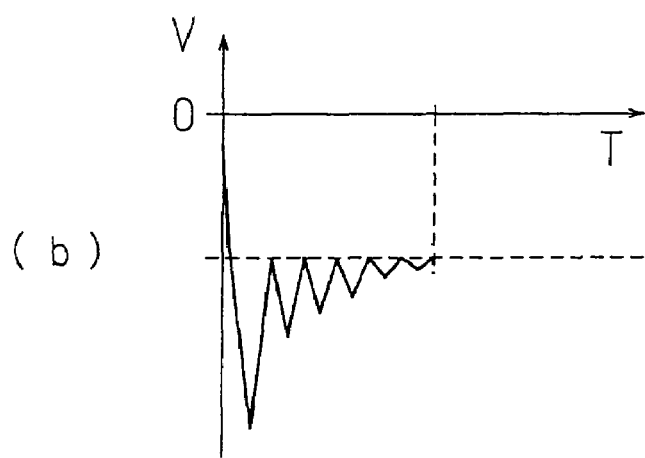
Figure 17:
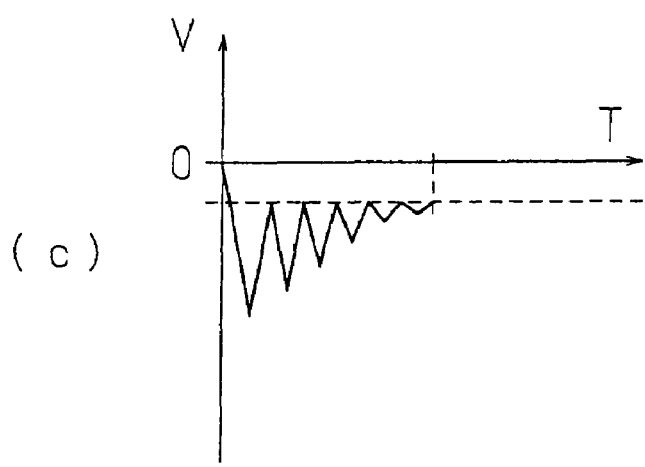

Next, the following description will explain the application of a voltage to the ion generator (ion generating element 1) of the present invention. FIG. 16 is an essential circuit diagram for use in the ion generator, and FIG. 17 is an applied voltage waveform view when a voltage was applied to the ion generating element 1 by using the circuit of FIG. 16.

In FIG. 16, the numeral 80 represents an AC commercial power supply, and is connected to point P that is one input terminal of high-voltage applying means 90 through an SSR (solid state relay). In contrast to point P to which the SSR is connected, point Q that is the other input terminal of the high-voltage applying means 90 is directly connected to the AC commercial power supply 80. Here, the point Q is grounded, i.e., a ground line.

The SSR is controlled to be open/closed by a control signal SS from a controller 83a of a microcomputer 83. Note that the control signal SS may be directly inputted by additionally providing direct input means such as an input button, instead of the microcomputer control. The SSR is connected to the anode side of a diode D3 through a resistor R1. The cathode side of the diode D3 is connected to the positive electrode side of a capacitor C2. Moreover, the negative electrode side of the capacitor C2 is connected to the AC commercial power supply 80 through a diode D1. When the SSR is ON, electric power is supplied to the high-voltage applying means 90 from the AC commercial power supply 80, and a high voltage (a voltage necessary for ion generation) is applied to the ion generating element 1 so as to generate ions. When the SSR is OFF, electric power is not supplied to the high-voltage applying means 90 from the AC commercial power supply 80 and a high voltage is not applied to the ion generating element 1, and consequently no ions are generated.

One end of a primary winding 81P of a switching transformer 81 is connected to the positive electrode side of the capacitor C2. The other end of the primary winding 81P of the switching transformer 81 is connected to the SCR. A capacitor C1, resistors R3, R4 and R5 constitute a gate control circuit for a SCR. The resistor R2 divides the voltage of the AC commercial power supply 80 together with the resistor R1, and applies a suitable voltage to the capacitor C2. The diodes D2 and D4 are provided to prevent a reverse flow. The switching transformer 81 comprises a secondary winding 81S on the secondary side, and the ion generating element 1 is connected to the secondary winding 81S. The ion generating element 1 comprises a pair of facing electrodes (discharge electrode 13 and induction electrode 14).

A series circuit composed of rectifying means and switching means is connected between one of the pair of electrodes (here, the discharge electrode 13) of the ion generating element 1 and the ground line (namely, point Q). The rectifying means has an anode and a cathode. Here, the rectifying means is made of a diode D5, and the anode is connected to the discharge electrode 13 side, while the cathode is connected to the ground line side. The switching means is made of a relay 82. A capacitor C3 as an electrostatic capacity is connected in parallel to the rectifying means, i.e., the diode D5.

The relay 82 is controlled to be open/closed (ON-OFF control) by a relay control signal 82S from the controller 83a of the microcomputer 83. The relay control signal 82S is outputted after suitably processing and judging various input information IN to an input unit 84 of the microcomputer 83. Various input information IN to the input unit 84 is, for example, operation mode specifying information from a control section through which the user can select an operation mode, and is the result of measuring the contamination degree of the peripheral environment by an environmental sensor (for example, a contamination sensor). The controller 83a is made of a control circuit for outputting a control signal, etc. Note that some components in the microcomputer 83, such as an arithmetic unit, are omitted.

In such a construction, when the SSR is turned ON, an alternating current is applied between the points P and Q. In a cycle where the electric potential at the point P is higher than the electric potential at the point Q, the capacitor C2 is charged (the SCR is kept OFF). Next, when the alternating current is reversed (a cycle where the electric potential at the point Q is higher than the electric potential at the point P), a voltage equal to or higher than a threshold voltage is applied between the gate and cathode of the SCR by the operation of the gate control circuit, and the SCR is turned ON. When the SCR is turned ON, the capacitor C2 is discharged, and the current flows in the route of capacitor C2→switching transformer 81 (primary winding 81P)→SCR→diode D1, and consequently an induction voltage is also generated on the secondary winding 81S of the switching transformer 81.

Since the ion generating element 1 is a pseudo capacitance load and resistance load, the secondary circuit of the switching transformer 81 is equivalent to an LCR oscillation circuit. After energy corresponding to energy charged in the primary-side capacitor C2 is also discharged and consumed on the secondary side, oscillation is stopped.

FIG. 17 is an electric potential waveform view of the ion generating element 1. The axis of ordinates shows voltage V, while the axis of abscissas indicates time T. The voltage value is about 5 to 7 kV in the peak (positive) to peak (negative) value of the maximum amplitude, and the oscillation period of the oscillation waveform is about 0.1 to 0.2 ms. This oscillation waveform is generated in a cycle corresponding to the frequency of the AC commercial power supply 80. FIG. 17(a) shows an electric potential waveform when the relay 82 in the circuit of FIG. 16 is in the OFF state (i.e., the state where the diode D5 is not connected), and substantially equal amounts of positive ions and negative ions are generated.

On the other hand, FIG. 17(b) shows an electric potential waveform when the capacitor C3 is removed from the circuit of FIG. 16 and the relay 82 is in the ON state (i.e., the state where the diode D5 is connected). Since the diode D5 cuts a current in one direction, the electric potential of the discharge electrode 13 becomes a waveform shifted in the negative direction when seen from the electric potential at point Q. Accordingly, ions are generated such that the ratio of positive ions is small and that of negative ions is large.

Furthermore, FIG. 17(c) shows an electric potential waveform when the relay 82 in the circuit of FIG. 16 is in the ON state (i.e., the state where the diode D5 is connected and the capacitor C3 is added in parallel to the diode D5). The electric potential of the discharge electrode 13 is shifted in the positive direction as compared to that shown in FIG. 17(b), and a small amount of positive ions are generated. When the electrostatic capacity of the capacitor C3 was 200 pF, 140,000 positive ions/cc and 380,000 negative ions/cc were measured.

In an ion generator with such a circuit structure, comprising rectifying means (diode D5) having an anode and a cathode; switching means (relay 82) connected in series to the rectifying means; and an electrostatic capacitance (capacitor C3) connected in parallel to the rectifying means, the anode side being connected to one electrode (discharge electrode 13), the cathode side being connected to a ground line provided on voltage applying means (high-voltage applying means 90), the rectifying means and the switching means are mounted on a substrate outside the common case 4, other than a substrate on which the voltage applying means is installed. In other words, in the circuit shown in FIG. 16, a circuit substrate 89 composed of the relay 82, diode D5 and capacitor C3 (hereinafter referred to as the relay substrate 89) is configured as a substrate other than the high-voltage applying means 90, and the relay substrate 89 is disposed outside the common case 4.

Note that the high-voltage applying means 90 is provided on the circuit substrate 3 inside the common case 4. The phrase "outside the common case 4" used here means a concept including both of the condition where the relay substrate 89 is held on the outside of the common case 4, and the condition where the relay substrate 89 is mounted on a structure other than the common case 4, for example, a part of an air conditioning apparatus in which the ion generator is mounted, without holding the relay substrate 89 on the common case 4.

Besides, in the case of an air purifier, for example, the circuit substrate 3 and the relay substrate 89 are constructed as different substrates, and the relay substrate 89 is mounted on a part of the air purifier, without being held by the common case 4.

Accordingly, since the substrate (relay substrate 89) having the rectifying means and switching means and the substrate (circuit substrate 3) with the voltage applying means mounted thereon can have a sufficient distance therebetween, it is possible to keep a long insulation distance, thereby enabling stable generation of substantially equal amounts of positive ions and negative ions.

INDUSTRIAL APPLICABILITY

As described above, according to the present invention, since the booster means, circuit substrate and ion generating element are configured as a unit by mounting them on the common case (housing), a compact configuration is achieved, and therefore the ion generator can be easily used in a wide range of application by its connection it to an external power supply and control circuit.

Moreover, with the use of the common case (housing) constructed as a box case having an opening in a part thereof and a rational arrangement where the ion generating element is mounted in the opening, the booster means is stored in the inner side of the common case, facing this, mounting section for the ion generating element, and the circuit substrate is supported therebetween, it is possible to achieve a further compact configuration.

Besides, since the volume specific resistance of the common case (housing) is set to be equal to or higher than $1 \times 10^{16}$ Ω·cm, or the common case (housing) is molded using a resin material containing no carbon, it is possible to ensure satisfactory insulation for the common case and generate positive ions and negative ions in a stable manner.

Moreover, the present invention uses a plate-like ion generating element comprising a discharge electrode and an induction electrode which face each other with a dielectric therebetween, and the ion generating element is mounted in a mounting section of the common case (housing) so that the discharge electrode side faces outward. It is therefore possible to achieve a further compact configuration, and efficiently generate positive ions and negative ions by plasma discharge from the discharge electrode.

Furthermore, since connecting means for external connection is provided integrally on the outside of the common case (housing), the ion generator can be readily connected to an external power supply and control circuit and easily used in various kinds of applications. In addition, since the mounting section for the ion generating element is provided on a surface substantially parallel to the connecting direction to such connecting means, it is possible to connect the connection terminals easily without causing the mounting section for the ion generating element to face downward, thereby preventing damages of the ion generating element.

The ion generator further comprises means for supporting the ion generating element in a state separated from the installation surface when the ion generator is installed with the mounting section for the ion generating element facing downward. Therefore, even when a mistaken installation takes place and the mounting section for the ion generating element faces downward in the mounting step including connection to an external power supply and control circuit, it is possible to prevent damages of the ion generating element due to contact with the installation surface.

Furthermore, since the ion generator is constructed by providing the mounting section for the ion generating element on the lid plate for closing the opening of the common case (housing) and mounting the ion generating element together with the lid plate, it is possible to obtain a satisfactory mounted state. In addition, since the window holes for passing the lead wires for connecting the ion generating element and the circuit substrate are formed in the lid plate and fastening parts for the lead wires are provided on the peripheral edges of the window holes, it is possible to readily connect the ion generating element and the circuit substrate without a trouble associated with running of the lead wires, and achieve satisfactory connections.

Besides, since the periphery of the booster means and the space between the circuit substrate and the ion generating element are insulation-molded with the fillers, it is possible to satisfactorily insulate them from each other under a high-pressure driving voltage and perform a stable operation. Additionally, since the volume specific resistance of the fillers is equal to or more than $1 \times 10^{13}$ Ω·cm, it is possible to generate positive ions and negative ions in a stable manner. Moreover, since the first filler to be put to the periphery of the booster means was selected by attaching great importance to the insulating strength, while the second filter to be put in between the circuit substrate and the ion generating element was selected by attaching great importance to the flowability, it is possible to obtain excellent insulating performances.

Furthermore, since the mounted components on the circuit substrate are received/stored in the receiving room provided beside the storing room for the booster means, it is possible to reduce the separation distance between the circuit substrate and the ion generating element without being interfered by the presence of the mounted components and achieve a further compact configuration. In addition, since the receiving room for the mounted components and the storing room for the booster means are separated from each other by a bulkhead, the filler for insulation molding will never intrude into the receiving room and stress will not be applied to the mounted components with the solidification and shrinkage of the filler, thereby preventing occurrence of damages and detachment and achieving an improvement in the yield.

Besides, since positive ions and negative ions generated by the ion generating element are cluster ions surrounded by a plurality of $H_2O$ molecules, it is possible to inactivate floating particles and disinfect floating bacteria in a space into which these ions are to be emitted, and thereby purifying the space satisfactorily.

The invention claimed is:

1. An ion generator comprising:
   an ion generating element for generating positive ions and negative ions by application of a driving voltage;
   booster means and a circuit substrate for generating a driving voltage to be applied to said ion generating element; and
   a housing having a storing room for said booster means, a supporting section for said circuit substrate and a mounting section for mounting said ion generating element therein,
   wherein said housing is a box case having an opening in a part thereof, and has said mounting section for said ion generating element in a periphery of said opening, said storing room for said booster means in an inner side of said housing, facing said mounting section, and said supporting section for said circuit substrate between said storing room and said mounting section.

2. The ion generator as set forth in claim 1, wherein a volume specific resistance of said housing is set to be not less than $1 \times 10^{16}$ Ω·cm.

3. The ion generator as set forth in claim 1, wherein said housing is molded using a resin material containing no carbon.

4. The ion generator as set forth in claim 1, wherein said ion generating element comprises a discharge electrode and an induction electrode that face each other with a dielectric there between, and said discharge electrode is mounted on said mounting section of said housing so that said discharge electrode faces outward.

5. The ion generator as set forth in claim 1, comprising connecting means for supplying electric power to said booster means, integrally on an outside of said housing.

6. The ion generator as set forth in claim 5,
   wherein said mounting section for said ion generating element is provided substantially in parallel to a connecting direction to said connecting means.

7. The ion generator as set forth in claim 1, comprising supporting means for supporting said ion generating element at a distance from a suitable installation surface when said ion generator is installed on the installation surface with said mounting section for said ion generating element facing downward.

8. The ion generator as set forth in claim 1,
   wherein said mounting section for said ion generating element is provided on a lid plate which is mounted to close the opening of said housing.

9. The ion generator as set forth in claim 8,
   wherein said ion generating element is connected to said circuit substrate with lead wires passing through window holes piercing said lid plate.

10. The ion generator as set forth in claim 9, comprising fastening parts for fastening said lead wires, on peripheral edges of said window holes.

11. The ion generator as set forth claim 1,
    wherein said booster means is insulation-molded with a first filler put in said storing room, while a space between said circuit substrate and said ion generating element is insulation-molded with a second filler put in there between.

12. The ion generator as set forth in claim 11,
    wherein a volume specific resistance of each of said first filler and second filler is set to be not less than $1 \times 10^{13}$ Ω·cm.

13. The ion generator as set forth in claim 11, wherein said first filler has a higher insulation strength than said second filler, while said second filler has a higher flowability than said first filler.

14. The ion generator as set forth in claim 11, comprising a receiving room, provided beside said storing room for said booster means, for receiving/storing mounted components on said circuit substrate supported by said supporting section.

15. The ion generator as set forth in claim 14, comprising a bulkhead for separating said receiving room and said storing room from each other so as to prevent intrusion of said first filler and second filler.

16. The ion generator as set forth in claim 1, wherein the positive ions are H+(H2O)m (m is a natural number).

17. The ion generator as set forth in claim 1, wherein the negative ions are O2−(H2O)n (n is a natural number).

18. An electric apparatus including an air passage for passing a flow of air, characterized by comprising an ion generator as set forth in claim 1, disposed in the middle of said air passage so that said mounting section for said ion generating element faces the flow of air.

19. An air conditioning apparatus characterized by comprising an ion generator as set forth in claim 1.

20. An ion generator comprising:
an ion generating element;
voltage booster;
a circuit board including a circuit operably connected to said ion generating element for generating a driving voltage; and
a housing having a first chamber for receiving said voltage booster, a support for said circuit board and a mount for said ion generating element,
wherein said housing comprises a case having an opening, a periphery of said opening comprising said mount, and a second chamber separated from said first chamber by a wall comprising said support.

21. The ion generator as set forth in claim 20, wherein a volume specific resistance of said housing is greater than or equal to $1 \times 10^{16}$ Ω·cm.

22. The ion generator as set forth in claim 20, wherein said housing comprises a carbonless resin material.

23. The ion generator as set forth in claim 20 including a first insulator comprising a first material in said first chamber and a second insulator comprising a second material disposed between said mount and said support.

24. The ion generator as set forth in claim 23, wherein said first insulator has a higher insulation strength than said second insulator, and said second insulator has a higher flowability than said first insulator.

25. An ion generator comprising:
a housing having an opening into a main chamber, said main chamber including a first subchamber having an opening facing and spaced from said housing opening and a peripheral edge and a second subchamber opening into said main chamber and having an opening facing and spaced from said housing opening and having a peripheral edge;
an ion generating element mounted in said main chamber;
a voltage booster in said first subchamber; and
a circuit board mounted in said main chamber and including at least one circuit element projecting into said second subchamber and operably connected to said ion generating element for generating a driving voltage.

26. The ion generator of claim 25 wherein said circuit board is mounted on said first subchamber peripheral edge and said second subchamber peripheral edge.

* * * * *